(12) United States Patent
Lehtinen et al.

(10) Patent No.: US 10,952,742 B2
(45) Date of Patent: Mar. 23, 2021

(54) SELF-ALIGNING PULLWIRE FOR RELOADABLE HEMOSTASIS CLIPPING DEVICE

(71) Applicant: BOSTON SCIENTIFIC SCIMED, INC., Maple Grove, MN (US)

(72) Inventors: Laurie A. Lehtinen, Marlborough, MA (US); Joseph W. King, Franklin, MA (US); Filip Adamowicz, Burlington, VT (US); Naroun Suon, Lawrence, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 221 days.

(21) Appl. No.: 16/189,880

(22) Filed: Nov. 13, 2018

(65) Prior Publication Data
US 2019/0159783 A1 May 30, 2019

Related U.S. Application Data
(60) Provisional application No. 62/591,611, filed on Nov. 28, 2017.

(51) Int. Cl.
*A61B 17/122* (2006.01)
*A61B 17/128* (2006.01)
(Continued)

(52) U.S. Cl.
CPC ........ *A61B 17/122* (2013.01); *A61B 17/1227* (2013.01); *A61B 17/1285* (2013.01);
(Continued)

(58) Field of Classification Search
None
See application file for complete search history.

(56) References Cited

U.S. PATENT DOCUMENTS

| | | | |
|---|---|---|---|
| 2005/0033312 A1* | 2/2005 | Suzuki | A61B 17/1285 606/110 |
| 2007/0282355 A1* | 12/2007 | Brown | A61B 17/122 606/151 |
| 2009/0163934 A1* | 6/2009 | Raschdorf, Jr. | A61B 17/00234 606/139 |

FOREIGN PATENT DOCUMENTS

| | | |
|---|---|---|
| EP | 2 113 208 | 11/2009 |
| JP | 2016-193003 | 11/2013 |

(Continued)

*Primary Examiner* — Shaun L David
(74) *Attorney, Agent, or Firm* — Fay Kaplun & Marcin, LLP

(57) ABSTRACT

A system and method for treating tissue includes an applicator including a bushing and a control member. The control member extends through the bushing to an enlarged distal end. The system also includes clip assembly releasably coupleable to the applicator. The clip assembly includes clip arms and a yoke including a distal portion connected to the clip arms and a proximal portion. The proximal portion includes a slot configured to receive the enlarged distal end of the control member and at least one helical cut positioned at a proximal end of the slot. The helical cut is configured to rotate the enlarged distal end from a first orientation in which the enlarged distal end is offset from the slot to a second orientation in which the enlarged distal end is aligned with the slot so that when a force thereon exceeds a threshold value, the enlarged distal end passes into the slot.

18 Claims, 4 Drawing Sheets

(51) Int. Cl.
*A61B 17/12* (2006.01)
*A61B 90/00* (2016.01)
*A61B 17/08* (2006.01)
*A61B 17/10* (2006.01)
*A61B 17/00* (2006.01)
*A61B 1/018* (2006.01)

(52) U.S. Cl.
CPC .............. *A61B 90/03* (2016.02); *A61B 1/018* (2013.01); *A61B 17/083* (2013.01); *A61B 17/10* (2013.01); *A61B 2017/00477* (2013.01); *A61B 2017/12004* (2013.01); *A61B 2090/034* (2016.02); *A61B 2090/037* (2016.02)

(56) References Cited

FOREIGN PATENT DOCUMENTS

| WO | 2003/030746 | 4/2003 |
|---|---|---|
| WO | 2007/142977 | 12/2007 |

\* cited by examiner

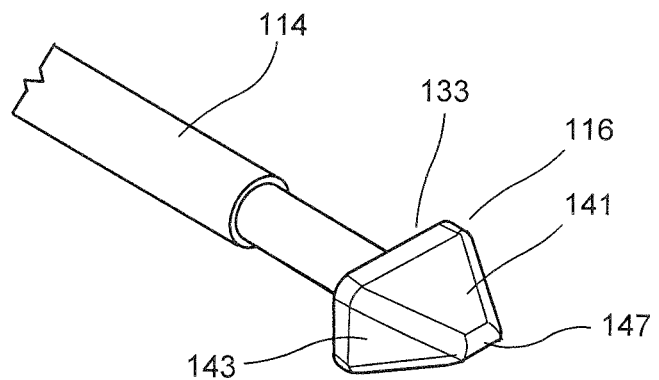
F I G. 7
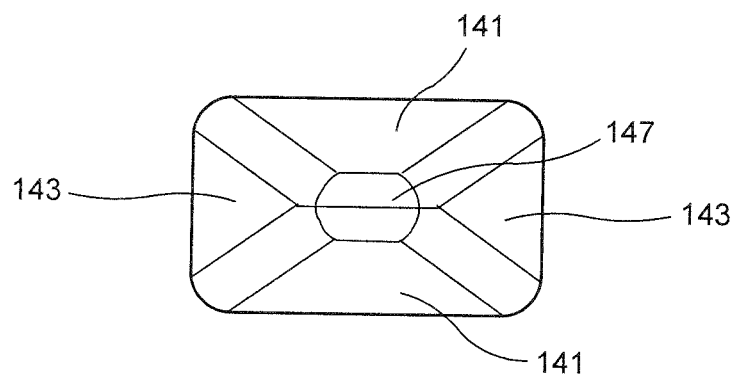
F I G. 8
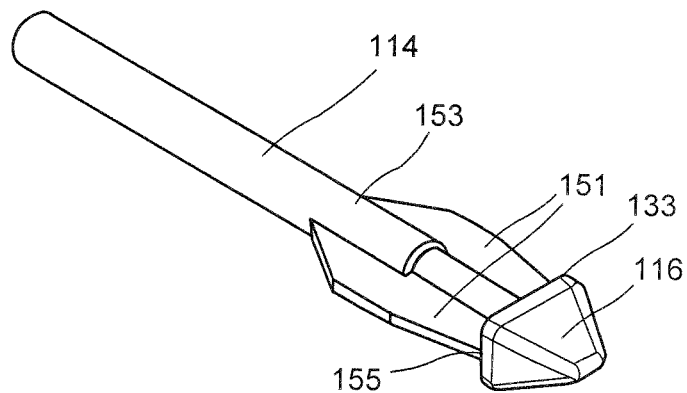
F I G. 9

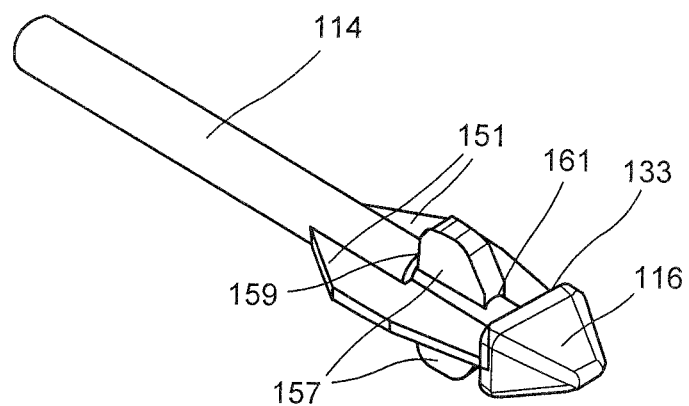
F I G. 10
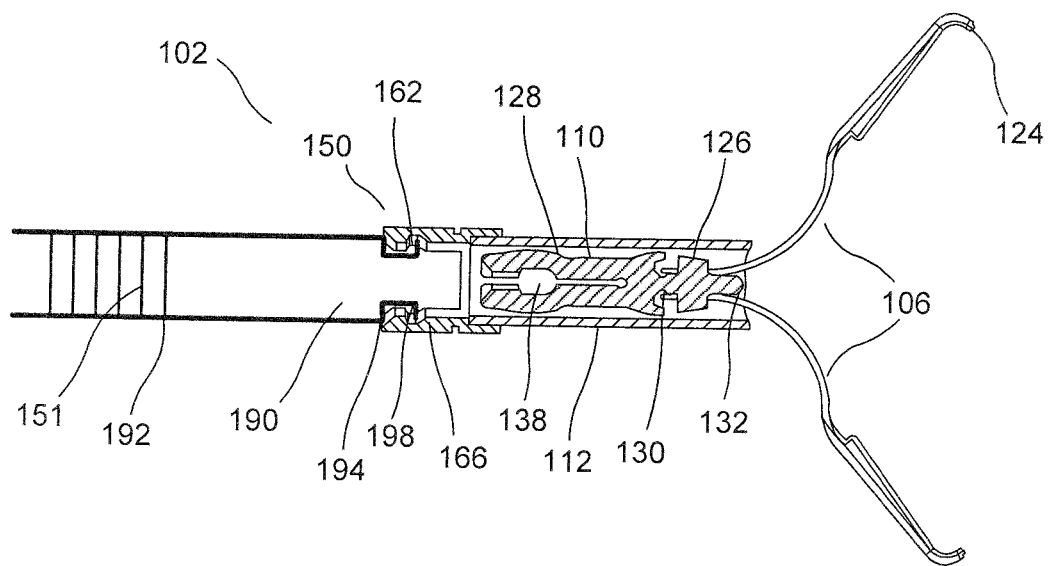
F I G. 11

SELF-ALIGNING PULLWIRE FOR RELOADABLE HEMOSTASIS CLIPPING DEVICE

PRIORITY CLAIM

The present disclosure claims priority to U.S. Provisional Patent Application Ser. No. 62/591,611 filed Nov. 28, 2017; the disclosure of which is incorporated herewith by reference.

FIELD OF INVENTION

The present invention relates to compression clips, and more specifically, to compression clips delivered to a target site through an endoscope to cause hemostasis of blood vessels located along the gastrointestinal tract.

BACKGROUND INFORMATION

Pathologies of the gastrointestinal (GI) system, the biliary tree, the vascular system, and other body lumens and hollow organs are often treated through endoscopic procedures, many of which require hemostasis to control internal bleeding. Hemostasis clips grasp tissue surrounding a wound and temporarily hold edges of the wound together to allow natural healing processes to permanently close the wound. Specialized endoscopic clipping devices are used to deliver the clips at the desired locations within the body after which the clip delivery device is withdrawn, leaving the clip within the body.

SUMMARY

The present disclosure relates to a system for treating tissue. The system includes an applicator including a bushing and a control member, the control member extending through the bushing to an enlarged distal end and a clip assembly releasably coupleable to the applicator, the clip assembly including clip arms extending from a proximal end to a distal end, proximal ends received within a channel of a capsule to be moved between a tissue receiving configuration, in which distal ends of the clip arms are separated from one another, and a tissue clipping configuration, in which distal ends of the clip arms are moved toward one another and a yoke including a distal portion connected to the clip arms and a proximal portion, the proximal portion including a slot configured to receive the enlarged distal end of the control member and at least one helical cut positioned at a proximal end of the slot, the helical cut configured to rotate the enlarged distal end from a first orientation in which the enlarged distal end is offset from the slot to a second orientation in which the enlarged distal end is aligned with the slot so that when a force thereon exceeds a threshold value, the enlarged distal end passes into the slot.

In an embodiment, the enlarged distal end is substantially pyramidal in shape, the enlarged distal end tapering from a rectangular, substantially planar, proximal face to a distal tip.

In an embodiment, the yoke is configured to be deformed when a force exerted thereon by the enlarged distal end exceeds a predetermined threshold value.

In an embodiment, the yoke includes opposed portions biased toward one another and defining the slot therebetween, the opposed portions spreading apart to permit the enlarged distal end to be passed distally into the slot.

In an embodiment, the yoke includes a second helical cut positioned at the proximal end of the slot.

In an embodiment, the first helical cut is positioned on a first one of the opposed portions and second helical cut is positioned on a second one of the opposed portions, the first and second helical cuts being open to the slot.

In an embodiment, the first and second helical cuts extend in the same helical direction so that each of the first and second cuts rotate the enlarged distal end in the same direction.

In an embodiment, the proximal and distal portions of the yoke are connected to one another via a frangible link designed to fail when a force exerted thereon exceeds a predetermined threshold value.

The present disclosure also relates to a reloadable clipping device. The device includes a clip assembly including a pair of clip arms, each of the clip arms extending from a proximal end to a distal end, proximal ends of the clip arms slidably received within a channel of a capsule to be moved between a tissue receiving configuration, in which distal ends of the clip arms are separated from one another, and a tissue clipping configuration, in which distal ends of the clip arms are moved toward one another, an applicator including a catheter and a control member extending therethrough, the control member including an enlarged distal end configured to be connected to the clip arms to move the clip assembly between the tissue receiving configuration and the tissue clipping configuration, and a yoke including a slot configured to receive the enlarged distal end of the control member and at least one helical cut positioned at a proximal end of the slot, the helical cut configured to rotate the enlarged distal end from a first orientation in which the enlarged distal end is offset from the slot to a second orientation in which the enlarged distal end is aligned with the slot so that when a force thereon exceeds a threshold value, the enlarged distal end passes into the slot.

In an embodiment, the yoke includes first and second opposed portions biased toward one another and defining the slot therebetween, the first and second opposed portions spreading apart to permit the enlarged distal end to be passed distally into the slot.

In an embodiment, the yoke includes second, third and fourth helical cuts.

In an embodiment, the first and second helical cuts are formed on an inner surface of the first opposed portion open to the slot and the third and fourth helical cuts are formed on an inner surface of the second opposed portion open to the slot, the first and third helical cuts extending in a first helical direction to rotated the enlarged distal end in the first helical direction and the second and fourth helical cuts extending in a second, opposing, helical direction to rotate the enlarged distal end in the second helical direction.

In an embodiment, the enlarged distal end is substantially pyramidal in shape, the enlarged distal end tapering from a rectangular, substantially planar, proximal face to a distal tip.

In an embodiment, the control member includes a pair of substantially planar lateral fins extending from proximal ends to distal ends at a proximal end of the enlarged distal end, the lateral fins sized and shaped to fit within a proximal portion of the slot when the enlarged distal end is inserted therein.

In an embodiment, the control member includes a pair of substantially planar second fins extending from proximal ends to distal ends, the second fins being separated from the lateral fins, about the circumference of the control member, by approximately 90 degrees.

The present disclosure also relates to a method for treating tissue. The method includes loading a first clip assembly on an applicator by pressing an enlarged distal end of a control member of an applicator distally against a yoke connected to proximal ends of clip arms so that a helical cut in a proximal end of the yoke rotates the enlarged distal end from a first orientation in which the enlarged distal end is offset from a slot extending through the yoke configured to receive the enlarged distal end to a second orientation in which the enlarged distal end is aligned with the slot so that a further distal force on the control member causes the yoke to deform and the enlarged distal end to be received within the slot, inserting the loaded clip assembly to a target site within a living body via a working channel of an endoscope, moving the clip assembly between a tissue receiving configuration, in which the ends of the first clip arms are separated from one another, and a tissue clipping configuration, in which distal ends of the clip arms are moved toward on another, by moving the control member proximally relative to the applicator until a target tissue is gripped therebetween and releasing the clip assembly from the applicator by drawing the control member proximally relative to the clip arms, beyond a predetermined threshold value, so that a link in the yoke fails, separating the control member from the clip arms.

In an embodiment, the enlarged distal end is substantially pyramidal in shape, the enlarged distal end tapering from a rectangular, substantially planar, proximal face to a distal tip.

In an embodiment, loading the clip assembly on the applicator includes releasably coupling a catheter of the applicator to a capsule of the clip assembly via a coupler that is attached to a proximal end of the capsule.

In an embodiment, the yoke includes opposed portions biased toward one another and defining the slot therebetween, the opposed portions spreading apart to permit the enlarged distal end to be passed distally into the slot.

In an embodiment, the yoke further includes a second helical cut, the first helical cut being positioned on a first one of the opposed portions and the second helical cut being positioned on a second one of the opposed portions, the first and second helical cuts being open to the slot.

BRIEF DESCRIPTION

FIG. 7 shows a perspective view of an enlarged distal end of the control member of the system of FIG. 1;

FIG. 8 shows a front view of the enlarged distal end of the control member of the system of FIG. 1;

FIG. 9 shows a perspective view of an enlarged distal end of the control member of the system of FIG. 1 according to a second exemplary embodiment;

FIG. 10 shows a perspective view of an enlarged distal end of the control member of the system of FIG. 1 according to a third exemplary embodiment; and FIG. 11 shows a longitudinal cross-sectional view of the clip system of FIG. 1 according to another exemplary embodiment of the present disclosure.

DETAILED DESCRIPTION

Figure 1:
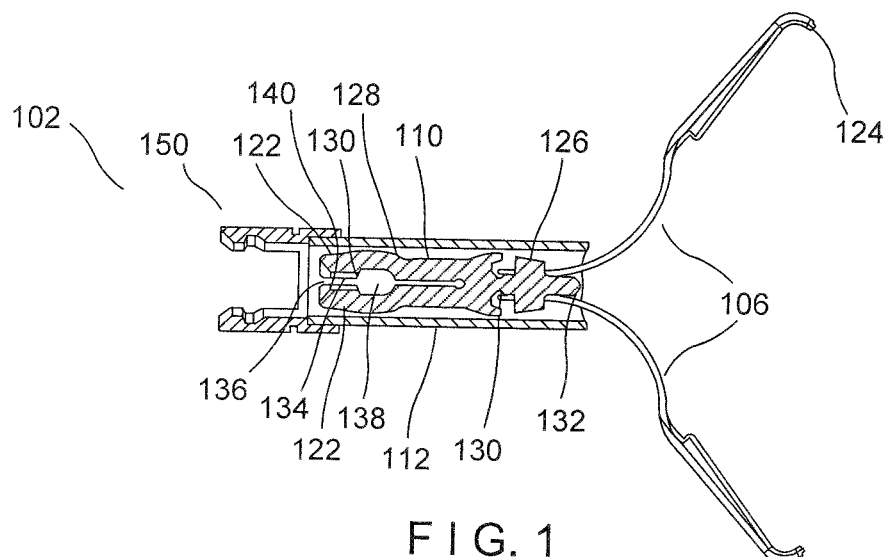
FIG. 1 shows a longitudinal cross-sectional view of a clipping system according to an exemplary embodiment of the present disclosure.

The present disclosure may be further understood with reference to the following description and the appended drawings, wherein like elements are referred to with the same reference numerals. The present disclosure relates to a clipping system and, in particular, relates to a reloadable endoscopic clipping system. Exemplary embodiments of the present disclosure describe a clip assembly that may be loaded onto a distal end of an applicator assembly prior to or during an endoscopic procedure. Once a clip has been deployed at a desired target area in the body, the applicator assembly may be reloaded with a new clip. In particular, the clipping system includes a control member with an enlarged distal end configured to self-align with a yoke from any orientation. The yoke is coupled to the enlarged distal end of the control wire via opposed portions which are spreadable to permit the enlarged distal end of the control member to be received therein. The unique geometry of the yoke and the control wire allow the control wire tip to be loaded into the yoke through this self-alignment without compromising clip loading and performance.

Figure 2:
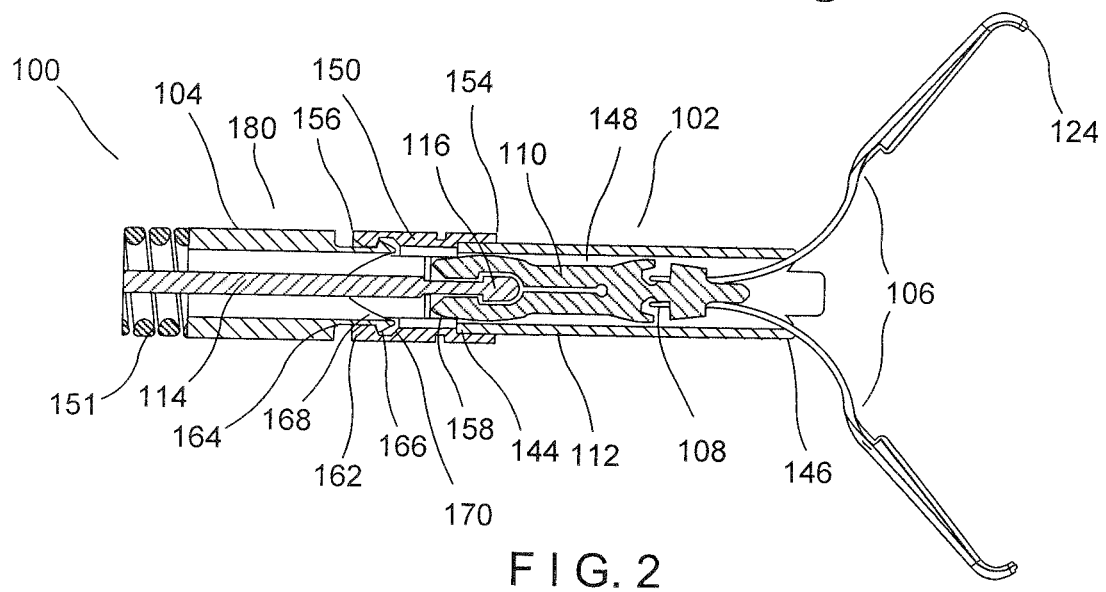
FIG. 2 shows another longitudinal cross-sectional view of the system of FIG. 1.

As shown in FIGS. 1-2, a system 100 according to an exemplary embodiment of the present disclosure comprises a clip assembly 102 loadable onto an applicator 104 prior to insertion of the system 100 into a living body for the clipping of target tissue. The applicator 104 is configured such that, after deployment of the clip assembly 102 in the living body, a new clip assembly 102 may be loaded onto the applicator 104 so that the same applicator 104 may be used to deliver a new clip assembly 102 to a second portion of target tissue in the living body. This process may be repeated until a desired number of clip assemblies 102 have been deployed. Each clip assembly 102 according to this embodiment comprises a pair of clip arms 106, proximal ends 108 of which are coupled to a yoke 110 slidably received within a capsule 112 so that the clip arms 106 are movable between an open tissue receiving configuration and a closed tissue clipping configuration. The yoke 110 is configured to receive an enlarged distal end 116 of a control member 114 such as, for example, a pullwire of an applicator 104 so that longitudinal movement of the control member 114 relative to the capsule 112 moves the clip arms 106 between the tissue receiving and tissue clipping configurations. In particular, the geometry of the yoke 110 and the distal end 116 of the control member 114 in the present embodiments allow a larger control member 114 tip to be loaded into the yoke 110 to increase an area of contact between the yoke 110 and the distal end 116 of the control member 114 to improve torque transmission from the control member 114 to the clip assembly 102 and eliminate the possibility of slippage. In use, once the clip assembly 102 has been used to clip a target tissue, the control member 114 is drawn proximally relative to the applicator 104 until a predetermined threshold force is exceeded, breaking the yoke 110 to deploy the clip assembly 102 in the body.

As described above, the clip assembly 102 includes the pair of clip arms 106, the proximal ends 108 of which are coupled to the yoke 110 which is slidably received within the capsule 112. Each of the clip arms 106 extends from a proximal end 108 connected to the yoke 110 to a distal end 124. The yoke 110 is configured to be connected to the control member 114 so that, when the yoke 110 and the control member 114 are connected, the control member 114 may be moved longitudinally with respect to the capsule 112 to move the clip assembly 102 between the tissue receiving and the tissue clipping configurations. The clip arms 106 of this embodiment are biased toward the open tissue receiving configuration so that, when moved distally out of the capsule 112, they spring to the open, tissue receiving configuration. In the tissue receiving configuration, distal ends 124 of the clip arms 106 are spread apart from one another to receive tissue therebetween. When the clip arms 106 are drawn into the capsule 112, the capsule 112 constrains the clip arms 106, drawing the distal ends 124 thereof together and holding them in the tissue clipping configuration.

The clip arms 106 may include optional gripping features configured to facilitate the gripping of tissue therebetween. For example, the distal ends 124 of the clip arms 106 may include tips extending laterally inward toward one another and/or teeth, protrusions, spikes or other structures configured to grip tissue between the distal ends 124 of the clip arms 106. The clip arms 106 may also include a locking feature configured to lock the clip arms 106 in the tissue gripping configuration, once target tissue has been gripped via the clip arms 106. In one embodiment, the clip arms 106 include a locking tab extending laterally outward therefrom. This locking tab is configured to engage a portion of the capsule 112 when the clip arms 106 have been drawn into the capsule 112 by a predetermined distance. For example, the locking tabs may be received within correspondingly sized, shaped and positioned locking windows extending laterally through a wall of the capsule 112 to lock the clip arms 106 relative to the capsule 112, in the tissue gripping configuration.

In one embodiment, the proximal ends 108 of the clip arms 106 are connected to one another to form one integral piece which is connected to the yoke 110. In another embodiment, the proximal ends 108 may be separate elements connected to one another via the yoke 110. The yoke 110 includes a distal portion 126 configured to be connected to the clip arms 106 and a proximal portion 128 configured to be connected to the enlarged distal end 116 of the control member 114. The distal and proximal portions 126, 128 of the yoke 110 of this embodiment are connected to one another via a link 130 that is configured to decouple when a force exerted thereon exceeds a predetermined threshold value. The link 130 may include, for example, a weakened portion of the yoke 110 formed via a taper, a notch, a recess or other structure decreasing a cross-sectional area of the yoke 110 therealong. In this embodiment, the distal and proximal portions 126, 128 are integrally formed of a single piece of material. In another embodiment, the link 130 may include a weld, adhesive or other coupling connecting the distal and proximal portions 126, 128. In this embodiment, the distal and proximal portions 126, 128 may be two separate elements coupled to one another via the link 130.

The distal portion 126 may be connected to the arms 106 in any variety of ways. In one example, the distal portion 126 is received within a correspondingly sized and shaped space 132 at a proximal end of the clip arms 106 such that when the distal portion 126 is received within the space 132, the yoke 110 is substantially fixed relative thereto. Thus, movement of the yoke 110 correspondingly moves the clip arms 106.

The proximal portion 128 is configured to be connected to the distal end 116 of the control member 114 of the applicator 104 via opposed portions 122 defining a longitudinal slot 134 extending from a proximal opening 136 at a proximal end of the yoke 110 along a longitudinal axis of the yoke 110 to a distal portion 138 sized and shaped to receive the enlarged distal end 116. A proximal portion 140 of the slot 134 extending between the proximal opening 136 and the distal portion 138 has a cross-sectional area (e.g., diameter) smaller than a cross-sectional area of the distal portion 138. The opposed portions are spreadable to receive the enlarged distal end 116 and biased toward one another so that, once the enlarged distal end 116 has passed distally into the distal portion 138 of the longitudinal slot 134, the opposed portions 122 of the proximal portion 128 spring back to lock the enlarged distal end 116 in the distal portion 138, coupling the control member 114 to the yoke 110. Thus, longitudinal movement of the control member 114 relative to the capsule 112 may control movement of the clip arms 106 between the tissue receiving and the tissue clipping configurations.

According to this embodiment, the enlarged distal end 116 of the control member 114 may be inserted into the distal portion 138 of the slot 134 via the proximal opening 136 of the yoke 110. When the enlarged distal end 116 is pushed distally into the yoke 110 with a force greater than a predetermined threshold value, the proximal portion 140 of the slot 134 deforms to permit the enlarged distal end 116 to pass therethrough into the distal portion 138. In other words, opposed portions 122 separate from one another from a distance sufficient to permit the enlarged distal end 116 to move distally therepast through the proximal portion 140 and into the distal portion 138. Once the enlarged distal end 116 has been received within the distal portion 138, the proximal portion 140 reverts to its original size, locking the enlarged distal end 116 of the control member 114 in the distal portion 138. In one embodiment, the proximal portion 140 of the slot 134 includes one or more features facilitating passage of the enlarged distal end 116 distally therepast, as described in further detail below. Once the enlarged distal end 116 of the control member 114 is received within the distal portion 138 of the longitudinal slot 134, the enlarged distal end 116 is prevented from moving proximally out of the distal portion 138 via a proximal shoulder 130 of the distal portion 138.

Figure 4:
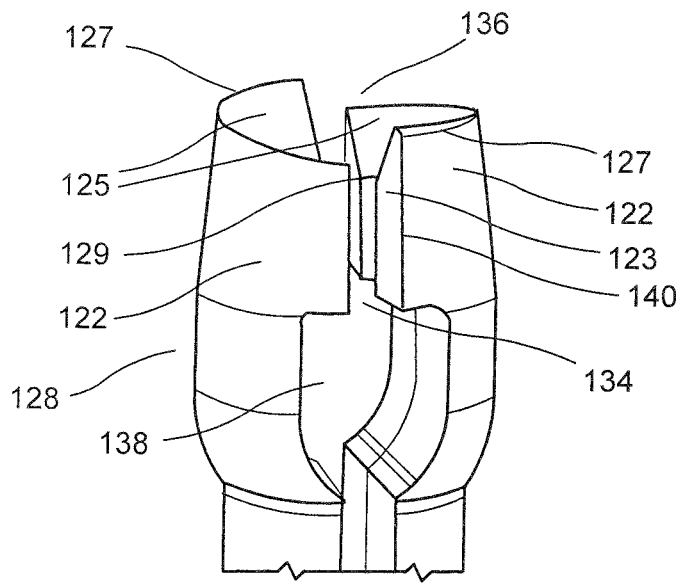
FIG. 4 shows a perspective view of a proximal end of a yoke of the system of FIG. 1 according to an exemplary embodiment.

In an exemplary embodiment depicted in FIG. 4, the opposed portions 122 include helically cut surfaces which allow the enlarged distal end 116 of the control member 114 to be inserted therein from any orientation without significantly increasing the loading force. Specifically, the helical cut of the proximal portion 140 forces the enlarged distal end 116 to self-align, eliminating additional steps in the process of loading a new clip assembly. As can be seen in FIG. 4, a cut or groove 125 is formed in the internal wall 123 of each of the opposed portions 122. The helical grooves 125 extend from the proximal surface 127 of the proximal portion 128 along a helical path towards a distal point 129. The helical grooves 125 have a conical lead-in taper and a substantially triangular cross-section that is swept along a helical spiral. The helical grooves 125 taper from the proximal surface 127 to the distal point 129. The depth of the helical groove may vary along the axial length of the proximal portion 128. For example, the distal end of the helical groove 125, at the distal point 129, is shallower than the proximal end of the helical groove 125. One of ordinary skill in the art will appreciate that the shape and size of the cross section of the helical groove may vary without departing from the scope of the present invention. Furthermore, the cross section of the helical grooves 125 may vary in size and shape without departing from the scope of the invention. For example, in other embodiments, the helical grooves 125 may have a V-shaped, parabolic, U-shaped, or semi-circle cross section. The helical grooves 125 are positioned at the proximal opening 136 to lead the enlarged distal end 116 into the proximal portion 140 of the slot 134. Each of the helical grooves 125 in the opposed portions 122 extends in the same helical direction so that the enlarged distal end 116 is spun by each in the same direction as it is self-aligning. For example, each of the helical grooves 125 is configured to taper in a first direction so the enlarged distal end 116 rotates only in that direction. It would be understood by those skilled in the art that, because the enlarged distal end 116 spins in a single direction, the amount of rotation necessary for the distal end 116 to achieve the insertion configuration (i.e., with lateral faces 143 of the distal end 116 facing laterally outward) is less than 180 degrees.

Figure 5:
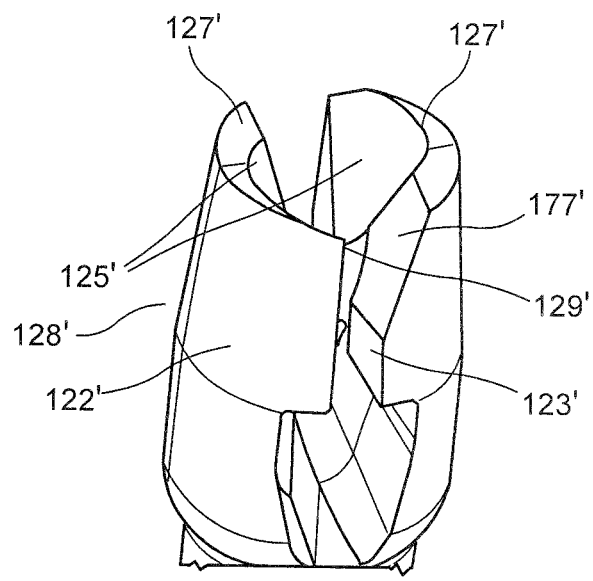
FIG. 5 shows a perspective view of a proximal end of a yoke of the system of FIG. 1 according to a second exemplary embodiment.

According to another exemplary embodiment the opposed portions 122' also include helically cut inner walls 123' which allow the enlarged distal end 116 of the control member 114 to be inserted therein from any orientation. However, in this embodiment, as can be seen in FIG. 5, the helical grooves 125' are axially longer than the helical grooves 125. That is, the length of the helical grooves 125' from the proximal surface 127' to the distal point 129' is greater than the length of the helical grooves 125, creating a longer taper in the proximal portion 128'. Furthermore, the angle of the helical grooves 125' is greater than the helical cuts 125. Similar to the helical cuts 125, each of the cuts 125' in the opposed portions 122' extend in the same helical direction so that the enlarged distal end 116 will spin in a single direction when self-aligning. For example, each of the cuts 125' tapers in a first direction so the enlarged distal end 116 rotates in a single desired direction as it is inserted. Additionally, a corner is cut off to create a non-helical angled surface 177' on each half of the yoke. This surface 177' helps open up more space for the distal end 116 to fit in its preferred orientation.

Figure 6:
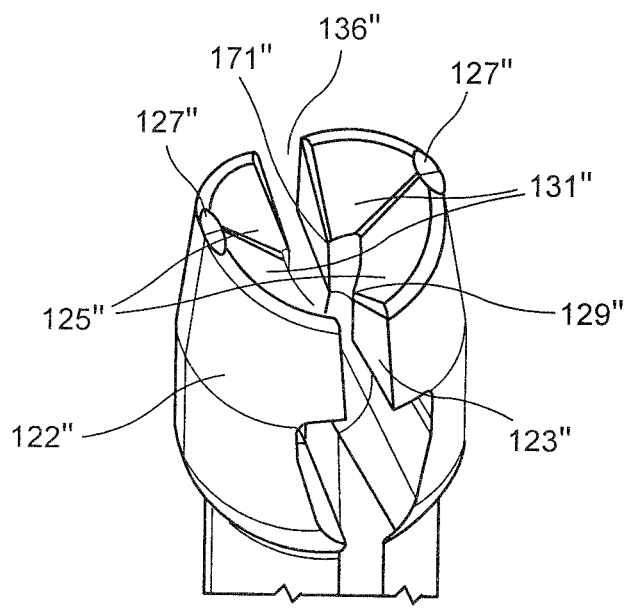
FIG. 6 shows a perspective view of a proximal end of a yoke of the system of FIG. 1 according to a third exemplary embodiment.

According to yet another exemplary embodiment, depicted in FIG. 6, each of the opposed portions 122" includes two helical cuts 125", 131" with paths extending in opposed directions. The opposing helical cuts 125", 131" of this embodiment allow the enlarged distal end 116 to rotate in either direction to achieve the insertion configuration. Thus, when control member 114 is inserted into the opening 136", the enlarged distal end 116 rotates less than 90 degrees to achieve the insertion configuration. As can be seen in FIG. 6, the helical grooves 125", 131" are cut into the internal wall 123" of each of the opposed portions 122". Each of the helical grooves 125", 131" extends from the proximal surface 127" of the proximal portion 128" along a helical path towards distal points 129", 171". However, as noted previously, the helical paths of the grooves 125", 131" extend in opposite directions—i.e., the helical grooves 125" are oriented to rotate the enlarged distal end 116 clockwise while helical grooves 131" are oriented to rotate the enlarged distal end 116 counterclockwise.

Figure 3:
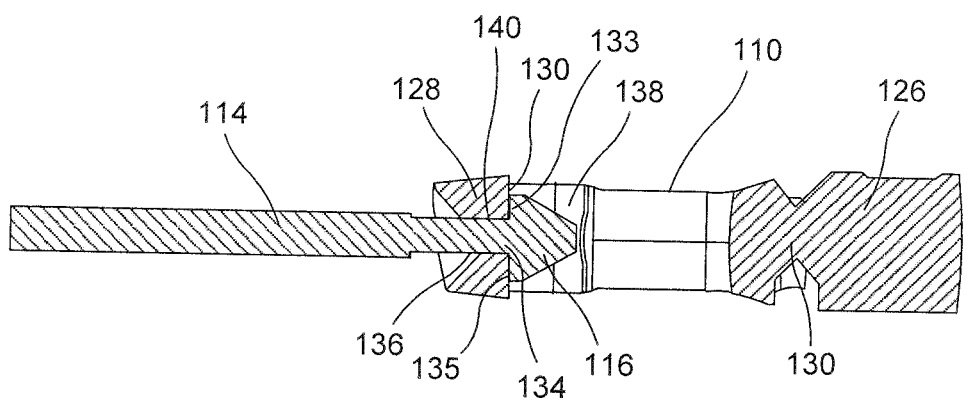
FIG. 3 shows a cross-sectional view of a yoke and distal end of a control member of the system of FIG. 1.

The enlarged distal end 116 of the control member 114, in this embodiment, has a substantially pyramidal shape extending from a rectangular proximal end and tapering to a distal tip. The pyramidal shape comprises two elongated triangular faces 141 separated by two shorter lateral faces 143, The distal tip 147 of the enlarged distal end 116 may also be rectangular in profile. This tapered shape facilitates distal insertion of the distal end 116 into the slot 134 of the yoke 110, but prevents disengagement therefrom once the distal end 116 has been received within the distal portion 138. For example, the proximal surface 133 of the distal end 116 is substantially planar so that, once the distal end 116 has been received within the distal portion 138, the proximal surface 133 engages a corresponding proximal surface 135 of the distal portion 138, as shown in FIG. 3. In other words, engagement between the planar proximal surfaces 133, 135 of the distal end 116 and the distal portion 138 of the slot 134, respectively, does not exert a radially outward force that might urge the opposed portions 122 to separate radially from one another. Thus, the distal end 116 is locked in the distal portion 138 and the distal end 116 does not pass back through the proximal portion 140 of the slot 134. The tapering pyramidal shape of the enlarged distal end 116 facilitates rotation of the enlarged distal end 116 when the outer surfaces of the distal end 116 come into contact with the helical cuts 125. As one skilled in the art would understand, the enlarged distal end 116 is configured to be inserted through the slot 134 in an insertion orientation with the lateral faces 143 facing laterally outward. However, if the enlarged distal end 116 contacts the proximal portion 128 of the yoke 110 in any other orientation, the helical cuts 125 rotate the distal end 116 toward the insertion orientation. The planar proximal surface 133 is sized and shaped to fit against the proximal surface 135 of the distal portion 138, the rectangular shape increasing the area of contacting surfaces on the control wire and clip and preventing any slipping of the enlarged distal end 116. Furthermore, because the rectangular proximal surface 133 corresponds to the shape of the proximal surfaces 135 of the distal portion 138, the tip mechanically interlocks with the proximal portion 128 of the yoke 110, improving the transmission of rotation from the control member to the yoke 110 and clip 102.

In another exemplary embodiment, the control member 114 includes a pair of lateral fins 151 to further increase an area of contact between the yoke 110 and the control member 114. As seen in FIG. 9, the fins 151 extend from a proximal end 153 to a distal end 155 at the proximal surface 133 of the enlarged distal tip 116. The fins 151 are substantially planar and have a thickness substantially equal to the width of the slot 134. Thus, when the enlarged distal end 116 is inserted through the slot 134 and into the distal portion 138, the 151 fins fit within the slot 134 of the yoke 110 between the distal portion 138 and the proximal opening 136. This increased contact between the control member 114 and the yoke 110 provided by the fins 151 helps with torque transmission from the control member 114 to the yoke 110 and further decreases the likelihood of slippage between the two components. The width of the fins 151 (i.e. the distance between the control member 114 and a lateral surface of the fins 151) in this embodiment is substantially equal to the width of the enlarged distal end 116. However, in this embodiment, the fins 151 include a proximal portion that tapers to the proximal end 153 of the fins 151. It will be understood that the fins 151 may take any shape so long as they fit within the slot 134 of the yoke 110 without causing the opposed portions 122 to be separated.

Looking to FIG. 10, the control member 114, in another exemplary embodiment, includes a second pair of fins 157 extending from a proximal end 159 to a distal end 161 configured to help center the control member 114 within the yoke 110. The fins 157 are separated from the fins 151, about the circumference of the control member 114, by approximately 90 degrees. In this embodiment the, fins 157 are substantially shorter than the fins 151 and are spaced away from the proximal surface 133 of the enlarged distal tip 116. Specifically, the fins 157 are configured to sit against the proximal surface of the yoke 110. Thus, the distance between the proximal surface 133 of the enlarged distal end 116 and the distal end 161 of the fins 157 is equal to or slightly larger than the length of the slot 134 between the proximal surface 135 of the distal portion 138 and the proximal surface 127. The fins 157 may be rounded to increase the surface area between the fins 157 and the rounded proximal surfaces of the yoke 110.

Turning back to FIG. 2, the capsule 112 extends from a proximal end 144 to a distal end 146 and includes a channel 148 extending longitudinally therethrough. The channel 148 is sized and shaped to slidably receive the yoke 110 and at least a proximal portion of the clip arms 106 therein. As described above, the capsule 112 may also include locking features (e.g., locking windows) for engaging corresponding locking features of a coupler 150 (e.g., locking tabs). In this embodiment, the proximal end 144 may be pre-assembled with a coupler 150. The capsule 112 may include a window extending laterally through the proximal end 144 thereof for receiving a correspondingly sized and shaped engaging feature of the coupler 150. In one embodiment, the capsule 112 includes a pair of diametrically opposed windows for engaging the coupler 150. It will be understood by those of skill in the art, however, that the capsule 112 may include any number of windows for receiving any number of corresponding engaging features of the coupler 150. It will also be understood by those of skill in the art that the coupler 150 may be pre-assembled with the capsule 112 via any one of a variety of couplings. In another example, laterally extending tabs on the proximal end 144 of the capsule 112 may be received within correspondingly sized and shaped windows of the coupler 150. In another example, the coupler 150 may be press fit onto the capsule 112 and/or adhered thereto via an adhesive.

The coupler 150 extends from a proximal end 154 to a distal end 156 and includes a channel 158 extending therethrough. The distal end 156 of the coupler 150 may be pre-assembled with the proximal end 144 of the capsule 112 so that the channel 158 of the coupler 150 is in communication with the channel 148 of the capsule 112. Thus, the control member 114 of the applicator 104 may be passed through the channels 158, 148 of the coupler 150 and the capsule 112, respectively, to be coupled to the yoke 110 during loading of the clip assembly 102. A proximal portion of the coupler 150 of this embodiment includes an engaging feature 162 configured to engage a bushing 180 (or catheter 190) of the applicator 104. For example, the coupler 150 may include a plurality of fingers 162. The fingers 162 are mounted over a distal end 164 of the bushing 180 so that the bushing 180 and the coupler 150 are snap fit together. The fingers 162 are biased toward an engaging configuration, but may be spread apart to permit the distal end 164 of the bushing 180 to be received therein. In particular, each of the fingers 162 includes a groove 166 extending along an interior surface thereof, the groove 166 is sized and shaped to receive a corresponding engaging feature 168 of at the distal end 164 of the bushing 180. The fingers 162 deflect away from one another as the engaging features 168 at the distal end 164 are being inserted therebetween. Once the engaging features 168 are received within the grooves 166, however, the fingers 162 snap inward under their natural bias so that the grooves 166 and the engaging features 168 engage one another, coupling the bushing 180 to the coupler 150. Each of the grooves 166 of this embodiment includes a tapered surface 170 tapering toward a distal end thereof. As will be described in further detail below, the tapered surfaces 170 are configured to interface with the engaging features 168 when a compressive force is applied thereto, causing the coupler 150 to yield to release the bushing 180 therefrom. A proximal interior edge 172 of each of the fingers 162 may also be angled, tapering toward a distal end thereof so that, when a portion of the coupler 150 comes into contact therewith, a further force may be exerted on the coupler 150.

The applicator 104 in this embodiment includes a bushing 180, a flexible member 181 extending proximally therefrom, and the control member 114 extending longitudinally through the flexible member 181 and the bushing 180. A proximal end of the flexible member 181 may be connected to a handle portion. The bushing 180 extends longitudinally from a proximal end connected to the flexible member to the distal end 164 configured to be releasably connected to the coupler 150. The control member 114 extends through the bushing 180 and the flexible member 181 from the enlarged distal end 116 to a proximal end connected to an actuator of the handle portion. The flexible member 181 may be formed as a coil or wire having sufficient flexibility to be passed through even tortuous paths of the living body and, in this embodiment, is sized and shaped to be passed through a working channel of an endoscope of other insertion device. The flexible member 181, however, may be formed of any other suitable flexible structure so long as the flexible member 181 is capable of providing a force in compression sufficient to counter the tension to be placed on the control member 114 from the clip assembly 102.

In another exemplary embodiment shown in FIG. 11, in lieu of a bushing 180, the applicator 104 may include a catheter 190. In this embodiment, the catheter 190 extends longitudinally from a proximal end 192 connected to the flexible member 181 to the distal end 194 configured to be releasably coupled to the coupler 150. The control member 114 extends through a lumen 196 of the catheter 190. A distal portion of the catheter 190 in this embodiment is sized and shaped to be inserted between the fingers 162 of the coupler 150 so that engaging features 198 at the distal end 194 of the catheter 190 are received and engaged with the grooves 166. In one embodiment, the engaging features 198 may be configured as tabs extending laterally outward (e.g., extending away from a longitudinal axis of the catheter 190) from the distal end 194. The tabs of the engaging features 198 may be sized and shaped to correspond to the grooves 166 so that when the tabs may be received with the grooves 166 via a snap fit.

The exemplary embodiments describe and show a capsule which abuts the bushing 180 when the clip assembly is moved from the tissue receiving to the tissue gripping configuration so that breakage/detachment of the distal portion 126 of the yoke 110 from the proximal portion 128 of the yoke 110 deploys the entire clip assembly. It will be understood by those of skill in the art, however, that the capsule 112 and bushing 180 may be releasably coupled to one another in any of a variety of ways. For example, in some embodiments, the capsule 112 may be released from the bushing 180 via breakage/detachment of the enlarged distal end 116 from a remaining portion of the control member 114, deploying the clip assembly.

Prior to being loaded on the applicator 104, the clip assembly 102 of the present disclosure may be housed in a cartridge. The cartridge may be configured as a storage container defining a space therewithin that is sized and shaped to house the clip assembly 102. The clip assembly 102 may be housed within the cartridge in the tissue receiving configuration. The cartridge includes a proximal opening through which a distal portion of the control member 114 and the bushing 180 or catheter 190 may be inserted to be coupled to the clip arms 106 and the capsule 112, respectively.

An exemplary method for loading the clip assembly 102 to the applicator 104 includes pushing the enlarged distal end 116 of the control member 114 distally against the yoke 110 of the clip assembly 102. When the enlarged distal end 116 contacts the proximal surface of the yoke 110, the pyramidal shape of the distal end 116 causes the distal end 116 to rotate until it reaches the correct orientation for insertion through the slot 134. Once the distal end 116 is correctly oriented, the distal three thereagainst continues until it exceeds a predetermined threshold value, causing opposed portions 122 of the yoke 110 to separate radially outward. Separation of the opposed portions 122 permits the enlarged distal end 116 to be passed through the proximal portion 136 and into the distal portion 138. Once the enlarged distal end 116 is received within the distal portion 138, the yoke 110 reverts to its original shape (e.g. under its natural bias), holding the enlarged distal end 116 therewithin. The bushing 180 may be moved distally to be coupled to the coupler 150 and capsule 112, either prior to the coupling of the control member 114 to the yoke 110 or after the coupling of the control member 114 and the yoke 110.

As described above, where the clip assembly 102 is housed within a cartridge, the bushing 180/catheter 190 and a distal portion of the control member 114 may be inserted through a proximal opening of the cartridge to be coupled to the clip assembly 102. Once the applicator 104 has been coupled to the clip assembly 102, as described, the clip assembly 102 may be removed from the cartridge by drawing the control member 114 proximally with respect to the bushing 180/catheter 190 to draw the clip arms 106 into the capsule 112, toward the insertion/tissue gripping configuration. Once the clip arms 106 are in the insertion/tissue gripping configuration, the entire applicator 104 may be moved proximally relative to the cartridge to draw the clip assembly 102 out of the cartridge via the proximal opening.

In use, after the clip assembly 102 has been loaded onto the applicator 104, the clip assembly 102 is inserted through a working channel of an endoscope (or any other insertion device) and inserted into the body (e.g., through a natural body lumen) to a site adjacent to a target portion of tissue to be clipped. The clip assembly 102 is inserted to the target tissue in the insertion configuration to facilitate its passage through the working channel. Upon reaching the site of the target tissue, the clip assembly 102 is advanced out of the distal end of the working channel and the clip arms 106 are extended out of the capsule 112 to move the clip arms 106 to the tissue receiving configuration. Once the target tissue has been received between the clip arms 106, the clip assembly 102 may be moved toward the tissue gripping configuration so that the target tissue is gripped between the distal ends 124 thereof. The clip arms 106 are moved toward the tissue gripping configuration by drawing the control member 114 proximally with respect to the bushing 180/catheter 190. Once the clip assembly 102 is in the tissue gripping configuration, the control member 114 may be drawn further proximally to lock the clip arms 106 with respect to the capsule 112.

To deploy the clip assembly 102, the control member 114 is drawn further proximally until the coupler 150 attached to the capsule 112 is drawn proximally against the bushing 180. The proximal motion of the coupler 150 causes the engaging features 168 of the bushing 180 to slide distally against the tapered surfaces 172 of the grooves 166, thereby deflecting the fingers 162 radially outward, out of engagement with the engagement features 168. In a further embodiment, the coupler 150 may be moved even further proximally relative to the bushing 180, resulting in even further deflection of the fingers 162. As described above, the coupler 150 may yield and/or fracture to release the bushing 180 therefrom.

Once the bushing 180 has disengaged from the coupler 150, the control member 114 is drawn even further proximally. Since the clip arms 106 are fixed with respect to the capsule 112 and the yoke 110 is prevented from releasing the enlarged distal end 116, the proximal motion of the control member 114 causes the distal end 116 of the control member 114 to exert a force on the yoke 110. When the force exerted on the yoke 110 exceeds a predetermined threshold value, the link 130 connecting the distal and proximal portions 126, 128 of the yoke 110 fails, separating the control member 114 (which is connected to the proximal portion 128) from the clip arms 106 (which are connected to the distal portion 126). As described above, the disengagement of the control member 114 from the clip arms 106 may also release the capsule 112 from the applicator 104. Thus, the applicator 104 may be withdrawn proximally from the body, leaving the clip assembly 102 clipped over the target tissue. Upon removal of the applicator 104 from the body, the proximal portion 128 of the yoke 110, which remains attached to the enlarged distal end 116 of the control member 114, may be removed therefrom by pulling the proximal portion 126 off of the distal end 116. When a force on the proximal portion 126 exceeds a predetermined threshold force, the longitudinal slot 134 yields or deforms to allow the enlarged distal end 116 to be removed therefrom. If so desired, a new clip assembly 102 is then loaded onto the applicator 104, in the same manner as described above, so that the system may then be used to clip a second portion of tissue. This process may be repeated using the same applicator 104 as many times as needed or desired.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiments disclosed, but rather modifications are also covered within the scope of the present invention as defined by the appended claims.

What is claimed is:

1. A system for treating tissue, comprising:
an applicator including a bushing and a control member, the control member extending through the bushing and including an enlarged distal end; and
a clip assembly releasably coupleable to the applicator, the clip assembly including:
clip arms extending from a proximal end to a distal end, proximal ends received within a channel of a capsule, the clip arms slidable relative to the capsule to be moved between a tissue receiving configuration, in which distal ends of the clip arms are separated from one another, and a tissue clipping configuration, in which distal ends of the clip arms are moved toward one another; and
a yoke including a distal portion connected to the clip arms and a proximal portion, the proximal portion including opposed portions defined via a slot, the opposed portions configured to be spread apart from one another to receive the enlarged distal end of the control member therebetween, a first one of the opposed portions including a first helical cut extending therealong, the first helical cut configured to rotate the enlarged distal end from a first orientation in which the enlarged distal end is offset from the slot to a second orientation in which the enlarged distal end is aligned with the slot so that when a force thereon exceeds a threshold value, the enlarged distal end causes the opposed portions to spread so that the enlarged distal end passes into the slot.

2. The system of claim 1, wherein the enlarged distal end is substantially pyramidal in shape, the enlarged distal end tapering from a rectangular, substantially planar, proximal face to a distal tip.

3. The system of claim 1, wherein the opposed portions of the yoke are biased toward one another and are deformed by spreading apart from one another when the enlarged distal end of the control member is pressed distally against the yoke.

4. The system of claim 1, wherein the yoke includes a second helical cut extending along a second one of the opposed portions.

5. The system of claim 4, wherein the first and second helical cuts are open to the slot.

6. The system of claim 4, wherein the first and second helical cuts extend in the same helical direction so that each of the first and second cuts rotate the enlarged distal end in the same direction.

7. The system of claim 1, wherein the proximal and distal portions of the yoke are connected to one another via a frangible link designed to fail when a force exerted thereon exceeds a predetermined threshold value.

8. A reloadable clipping device, comprising:
a clip assembly including a pair of clip arms, each of the clip arms extending from a proximal end to a distal end, proximal ends of the clip arms slidably received within a channel of a capsule to be moved between a tissue receiving configuration, in which distal ends of the clip arms are separated from one another, and a tissue clipping configuration, in which distal ends of the clip arms are moved toward one another;
an applicator including a catheter and a control member extending therethrough, the control member including an enlarged distal end configured to be connected to the clip arms to move the clip assembly between the tissue receiving configuration and the tissue clipping configuration; and
a yoke including opposed portions defined via a slot, the opposed portions configured to be spread apart from one another to receive the enlarged distal end of the control member therebetween, a first one of the opposed portions including a first helical cut extending therealong, the first helical cut configured to rotate the enlarged distal end from a first orientation in which the enlarged distal end is offset from the slot to a second orientation in which the enlarged distal end is aligned with the slot so that when a force thereon exceeds a threshold value, the enlarged distal end causes the opposed portions to spread so that the enlarged distal end passes into the slot.

9. The system of claim 8, wherein the yoke includes first and second opposed portions biased toward one another so that when the enlarged distal end of the control member is pressed distally thereagainst, the first and second opposed portions spread apart to permit the enlarged distal end to be passed distally into the slot.

10. The system of claim 9, wherein the yoke includes second, third and fourth helical cuts.

11. The system of claim 10, wherein the first and second helical cuts are formed on an inner surface of the first opposed portion open to the slot and the third and fourth helical cuts are formed on an inner surface of the second opposed portion open to the slot, the first and third helical cuts extending in a first helical direction to rotated the enlarged distal end in the first helical direction and the second and fourth helical cuts extending in a second, opposing, helical direction to rotate the enlarged distal end in the second helical direction.

12. The system of claim 8, wherein the enlarged distal end is substantially pyramidal in shape, the enlarged distal end tapering from a rectangular, substantially planar, proximal face to a distal tip.

13. The system of claim 8, wherein the control member includes a pair of substantially planar lateral fins extending from proximal ends to distal ends at a proximal end of the enlarged distal end, the lateral fins sized and shaped to fit within a proximal portion of the slot when the enlarged distal end is inserted therein.

14. The system of claim 13, wherein the control member includes a pair of substantially planar second fins extending from proximal ends to distal ends, the second fins being separated from the lateral fins, about the circumference of the control member, by approximately 90 degrees.

15. A method for treating tissue, comprising:
loading a first clip assembly on an applicator by pressing an enlarged distal end of a control member of the applicator distally against a yoke connected to proximal ends of clip arms, the yoke including opposed portions defined via a slot and configured to spread apart from one another to receive the enlarged distal end therebetween, a first helical cut extending along a first one of the opposed portions to rotate the enlarged distal end from a first orientation, in which the enlarged distal end is offset from the slot to a second orientation, in which the enlarged distal end is aligned with the slot, so that a further distal force on the control member causes the yoke to deform and the enlarged distal end to be received within the slot;
inserting the loaded clip assembly to a target site within a living body via a working channel of an endoscope;
moving the clip assembly between a tissue receiving configuration, in which the ends of the first clip arms are separated from one another, and a tissue clipping configuration, in which distal ends of the clip arms are moved toward one another, by moving the control member proximally relative to the applicator until a target tissue is gripped therebetween; and
releasing the clip assembly from the applicator by drawing the control member proximally relative to the clip arms, beyond a predetermined threshold value, so that a link in the yoke fails, separating the control member from the clip arms.

16. The method of claim 15, wherein the enlarged distal end is substantially pyramidal in shape, the enlarged distal end tapering from a rectangular, substantially planar, proximal face to a distal tip.

17. The method of claim 15, wherein loading the clip assembly on the applicator includes releasably coupling a catheter of the applicator to a capsule of the clip assembly via a coupler that is attached to a proximal end of the capsule.

18. The method of claim 15, wherein the yoke further includes a second helical cut positioned on a second one of the opposed portions, the first and second helical cuts being open to the slot.

\* \* \* \* \*